United States Patent
Huang et al.

(10) Patent No.: US 10,543,092 B1
(45) Date of Patent: Jan. 28, 2020

(54) BONE IMPLANT (71) Applicant: METAL INDUSTRIES RESEARCH AND DEVELOPMENT CENTRE, Kaohsiung (TW)

(72) Inventors: Jian-Yuan Huang, Kaohsiung (TW); Chen-Chie Wang, Kaohsiung (TW); Shih-Hua Huang, Kaohsiung (TW)

(73) Assignee: METAL INDUSTRIES RESEARCH AND DEVELOPMENT CENTRE, Kaohsiung (TW)

( * ) Notice: Subject to any disclaimer, the term of this patent is extended or adjusted under 35 U.S.C. 154(b) by 0 days.

(21) Appl. No.: 16/228,961

(22) Filed: Dec. 21, 2018

(51) Int. Cl.
*A61F 2/30* (2006.01)
*A61L 27/38* (2006.01)
*A61F 2/28* (2006.01)
*A61F 2/46* (2006.01)

(52) U.S. Cl.
CPC ............ *A61F 2/28* (2013.01); *A61F 2/30756* (2013.01); *A61F 2/4618* (2013.01); *A61L 27/3852* (2013.01); *A61F 2002/30011* (2013.01); *A61F 2002/3092* (2013.01); *A61F 2002/30751* (2013.01); *A61F 2002/30757* (2013.01); *A61F 2002/30766* (2013.01); *A61F 2310/00371* (2013.01); *A61F 2310/00377* (2013.01); *A61F 2310/00383* (2013.01); *A61L 27/3817* (2013.01); *A61L 2430/06* (2013.01)

(58) Field of Classification Search
CPC ........ A61F 2/30756; A61F 2002/30766; A61F 2002/2835; A61F 2002/30751; A61F 2002/30761; A61F 2002/30759; A61L 27/3852; A61L 27/3654; A61L 27/3817; A61L 2430/06
See application file for complete search history.

(56) References Cited

U.S. PATENT DOCUMENTS 6,251,143 B1 * 6/2001 Schwartz ............. A61B 17/064
606/75

\* cited by examiner

*Primary Examiner* — Brian A Dukert
(74) *Attorney, Agent, or Firm* — Burris Law, PLLC (57) ABSTRACT

A bone implant adapted to be implanted in a bone structure having a bone tissue, a cartilage tissue, and being formed with a hole is provided. The bone implant includes a scaffold disposed in the hole for connecting with the bone tissue, a connecting layer disposed on the scaffold, and a porous surface layer. The connecting layer includes a bottom portion connected to the scaffold and an extension portion extending from the bottom portion and formed with a plurality of receiving chambers. The porous surface layer is connected to the extension portion and includes a plurality of filler portions respectively filling the receiving chambers, and a tissue-connecting portion configured for connecting with the cartilage tissue.

20 Claims, 6 Drawing Sheets

BONE IMPLANT

FIELD

The disclosure relates to a bone implant, and more particularly to a bone implant adapted for repairing a cartilage tissue of a bone structure.

BACKGROUND

A cartilage tissue of a vertebrate has certain physical properties such as slight elasticity and toughness, and is able to produce lubrication and cushioning effects when the vertebrate's joint is in active condition. Hence, movement of the vertebrate's joint can occur smoothly, and the cartilage tissue also provides support and protection to a bone tissue at the vertebrate's joint. The cartilage tissue is mainly composed of chondrocytes, a large amount of extracellular matrix including collagen and proteoglycan, and fibers.

Figure 1:
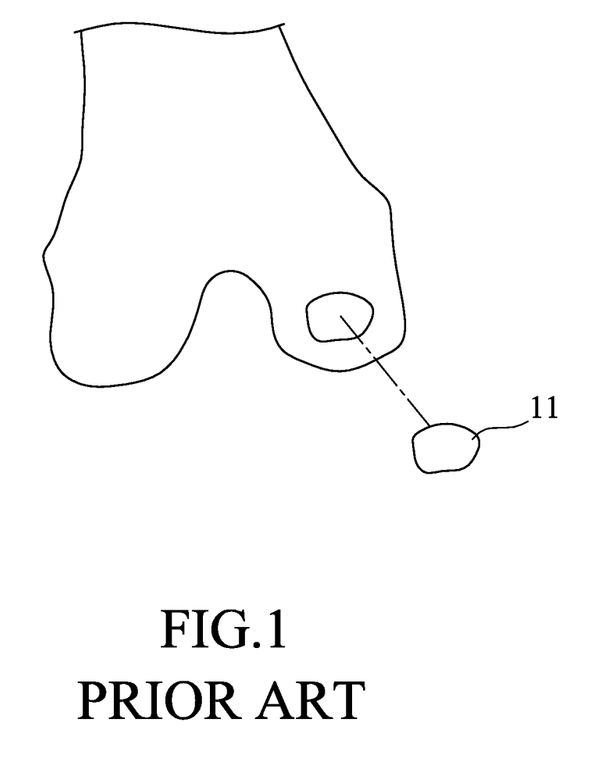
FIG. 1 is a schematic view illustrating a conventional therapeutic method for repairing a damaged cartilage tissue using a collagen membrane.

As shown in FIG. 1, when the cartilage tissue gets damaged due to long-term wear, a conventional therapeutic method to repair the damaged cartilage tissue is to fill a damaged portion of the cartilage tissue with a collagen membrane 11 having a shape complementary to the damaged portion. However, since the collagen membrane 11 filled in the damaged portion is not in connection with the bone tissue, the collagen membrane 11 cannot be securely fixed to the damaged portion of the cartilage tissue and may even be detached therefrom. That is, integration of the collagen membrane 11 into the damaged portion of the cartilage tissue of the injured part of a living body is relatively poor.

Figure 2:
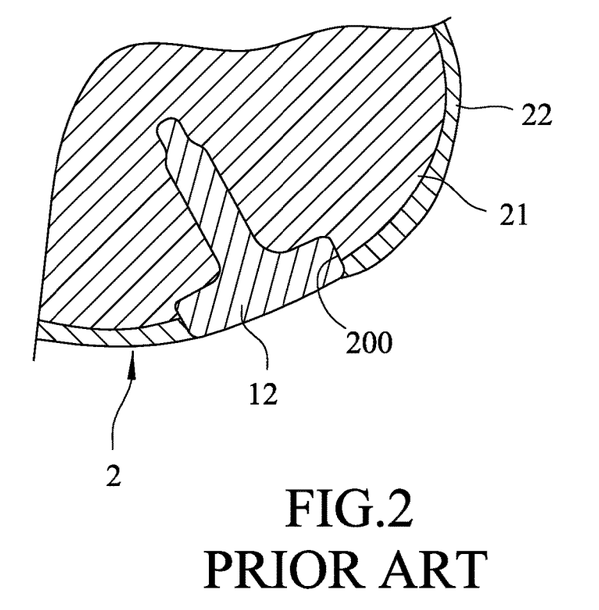
FIG. 2 is a cross-sectional view illustrating a conventional bone implant.

FIG. 2 illustrates a conventional bone implant 12 adapted for filling a damaged portion 200 of a bone 2. The bone 2 includes a bone tissue 21 and a cartilage tissue 22 wrapping the bone tissue 21. The conventional cartilage implant 12 not only fills the damaged portion 200 to repair the cartilage tissue 22, but also fixedly extends into the bone tissue 21 to enhance the fixing of the conventional bone implant 12 to the bone 2. However, the conventional bone implant 12 has only the cartilage repair function and still wears out after a long-term use. Besides, the conventional bone implant 12 is not sufficiently compatible with the cells of the bone 2, and thus is unable to provide regeneration function for the cartilage tissue. Furthermore, friction may be generated between the bone implant 12 and the portion of the cartilage tissue 22 around the bone implant 12, which may result in fibrosis and poor lubricity of the cartilage tissue 22.

Figure 3:
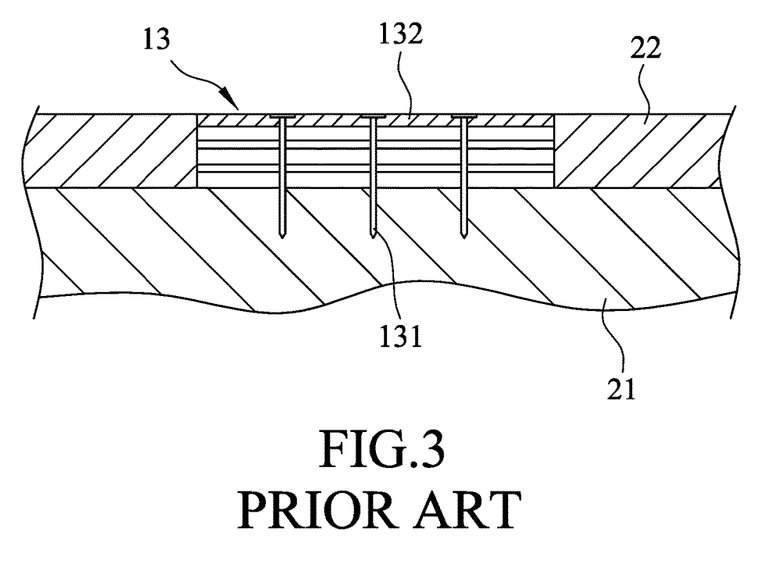
FIG. 3 is a cross-sectional view illustrating another conventional bone implant.

FIG. 3 shows another conventional bone implant 13 that includes at least one scaffold 131 disposed on a surface of the bone tissue 21 and connected to the cartilage tissue 22, and a chondrocyte layer 132 supported on the scaffold 131. By way of the chondrocyte layer 132, efficiency and success rate of repairing the cartilage tissue 22 can be improved. Although the conventional bone implant 13 has cartilage repair function, the scaffold 131 does not extend into the bone tissue 21 and is only connected to a portion of the cartilage tissue 22 adjacent thereto. Hence, bonding strength of the conventional bone implant 13 to the bone is being doubted. Besides, the cartilage tissue 22 is limited to a two-dimensional growth by extending along a surface of the cartilage tissue 22. Consequently, the cartilage tissue 22 may develop into a fibrous cartilage with poor lubricity instead of the expected hyaline cartilage with good lubricity.

SUMMARY

Therefore, an object of the disclosure is to provide a bone implant that can alleviate at least one of the drawbacks of the prior art.

According to the disclosure, a bone implant adapted to be implanted in a bone structure is provided. The bone structure includes a bone tissue and a cartilage tissue connected to the bone tissue, and is formed with a hole. The hole extends through the cartilage tissue and into the bone tissue and has an opening at the cartilage tissue. The bone implant includes a scaffold, a connecting layer, and a porous surface layer.

The scaffold is configured to be disposed in the hole of the bone structure for connecting with the bone tissue.

The connecting layer is disposed on the scaffold and proximal to the opening of the hole. The connecting layer includes a bottom portion that is connected to the scaffold, and an extension portion that extends from the bottom portion in a direction away from the scaffold and that is formed with a plurality of receiving chambers.

The porous surface layer is connected to the extension portion of the connecting layer. The porous surface layer includes a plurality of filler portions that respectively fill the receiving chambers, and a tissue-connecting portion that is connected to the filler portions and configured for connecting with the cartilage tissue.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Before the disclosure is described in greater detail, it should be noted that where considered appropriate, reference numerals or terminal portions of reference numerals have been repeated among the figures to indicate corresponding or analogous elements, which may optionally have similar characteristics.

Figure 4:
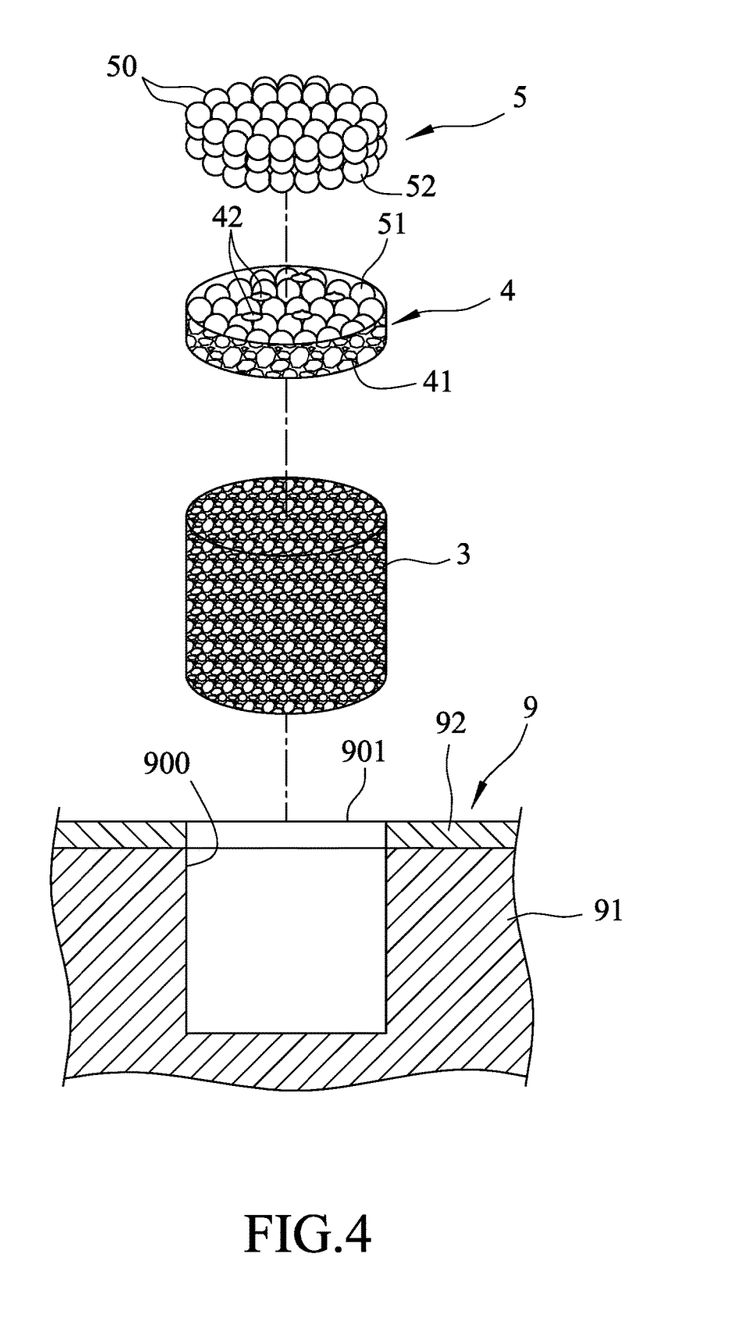
FIG. 4 is an exploded schematic view illustrating a first embodiment of a bone implant according to the disclosure.

Referring to FIG. 4, a first embodiment of a bone implant according to the disclosure is adapted to be implanted in a bone structure 9 of a living body. The bone structure 9 includes a bone tissue 91, and a cartilage tissue 92 connected to the bone tissue 91. The bone structure 9 is formed with a hole 900 extending into the bone tissue 91 through the cartilage tissue 92. The hole 900 has an opening 901 at the cartilage tissue 92. The first embodiment of the bone implant includes a scaffold 3, a connecting layer 4, and a porous surface layer 5.

The scaffold 3 is configured to be disposed in the hole 900 of the bone structure 9 for connecting with the bone tissue 91. The scaffold 3 may be made from one of a porous biomedical material and a porous biological material. The porous biomedical material and the porous biological material are biodegradable and biocompatible. In one form, the scaffold 3 has a porosity ranging from 40% to 70%. More specifically, the porosity of the scaffold 3 is 50%.

When the bone implant of the disclosure is implanted in the bone structure 9 of the living body, the scaffold 3 is able to connect to the bone tissue 91 with an enhanced stability due to the growth of osteoblasts of the bone tissue 9 and penetration of the grown osteoblasts into the scaffold 3. Moreover, a density of the scaffold 3 is adjustable through an adjustment in the porosity of the scaffold 3, and the biodegradability and the biocompatibility of the scaffold 3 facilitate degradation and absorption of the scaffold 3 by the living body with ease. The porous biomedical material may be selected from polymeric composite materials and bioceramics. The porous biological material may be an animal or human bone tissue.

Figure 5:
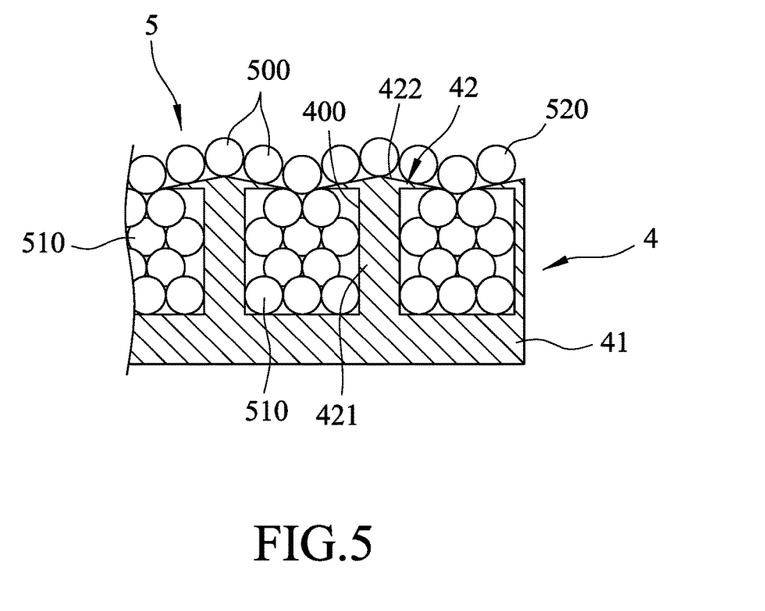
FIG. 5 is a fragmentary schematic view illustrating a connecting layer and a porous surface layer of the first embodiment.

Referring to FIG. 5, the connecting layer 4 is disposed on the scaffold 3 and is proximal to the opening 901 of the hole 900. The connecting layer 4 includes a bottom portion 41 that is connected to the scaffold 3, and an extension portion 42 that extends from the bottom portion 41 in a direction away from the scaffold 3 and that is formed with a plurality of receiving chambers 400. The extension portion 42 includes a plurality of spaced-apart rod sections 421 that respectively cooperate with said bottom portion 41 to define the receiving chambers 400, and a plurality of retaining sections 422. Each of the retaining sections 422 is connected to an end of a respective one of the rod sections 421 distal to the bottom portion 41. In the embodiment, each of the retaining sections 422 is barb-shaped, and each of the rod sections 421 and the corresponding retaining section 422 are integrally formed. The receiving chambers 400 may be spaced apart from each other or in spatial communication with each other. As with the scaffold 3, the connecting layer 4 may also be made from one of the porous biomedical material and the porous biological material. In one form, the scaffold 3 and the connecting layer 4 are made from the same material. The connecting layer 4 has a porosity ranging from 60% to 70%. More specifically, the porosity of the connecting layer 4 is 70%. Due to formation of the receiving chambers 400, the porosity of the connecting layer 4 is relatively good, which facilitates penetration of the porous surface layer 5 thereinto and thus, connection of the porous surface 5 therewith.

Figure 6:
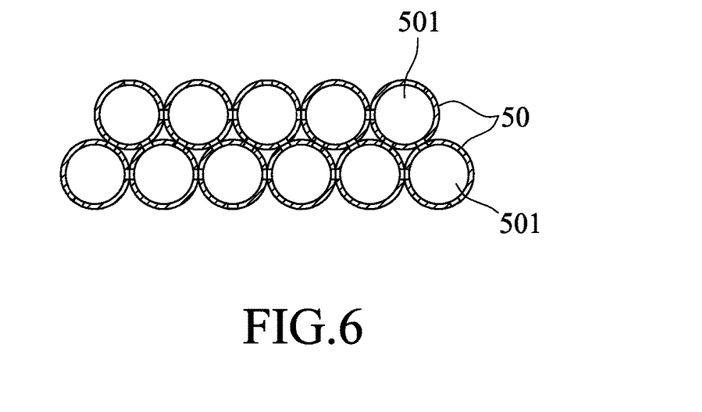
FIG. 6 is a fragmentary cross-sectional view illustrating the porous surface layer of FIG. 5.

The porous surface layer 5 is connected to the extension portion 42 of the connecting layer 4. The porous surface layer 5 includes a plurality of filler portions 51 that respectively fill the receiving chambers 400, and a tissue-connecting portion 52 that is connected to the filler portions 51 and configured for connecting with the cartilage tissue 92. Hence, an outer surface of the tissue-connecting portion 52 cooperates with an outer surface of the cartilage tissue 92 to form a continuous repaired cartilage-tissue surface. The tissue-connecting portion 52 and the filler portions 51 are made from the same material. In the embodiment, the porous surface layer 5 is composed of a plurality of stacked hollow microspheres 50. Referring to FIG. 6, each of the hollow microspheres 50 has an inner chamber 501. The inner chambers 501 of any two adjacent ones of the hollow microspheres 50 are in spatial communication with each other. In one form, each of the hollow microspheres 50 has a diameter ranging from 80 μm to 500 μm. The porous surface layer 5 may be made from a biomedical material selected from the group consisting of a polymeric material, gelatin, collagen, and combinations thereof.

The porous surface layer 5 composed of the stacked hollow microspheres 50 may be made by: forming a plurality of closed hollow microspheres 500 from the above-mentioned biomedical material; filling the receiving chambers 400 of the extension portion 42 of the connecting layer 4 with the closed hollow microspheres 500 until the closed hollow microspheres 500 overflow out, where a portion of the closed hollow microspheres 500 that are filled in the receiving chambers 400 are retain therein by the barb retaining sections 422 to form a plurality of preformed filling portions 510, and where another portion of the closed hollow microspheres 500 overflowing out of the receiving chambers 400 are stacked on the preformed filling portions 510 to form a preformed tissue-connecting portion 520; and vacuuming the closed hollow microspheres 500 to partially break the closed hollow microspheres 500 so as to form the stacked hollow microspheres 50. Through the vacuuming step, spatial communication between the inner chambers 501 of any two adjacent ones of the hollow microspheres 50 is established, and the hollow microspheres 50 in its entirety constitute a three-dimensional net-like structure.

It is noted that the retaining sections 422 of the connecting layer 4 are not limited to be barb-shaped, as long as the required effect of retaining the closed hollow microspheres 500 can be achieved.

Figure 7:
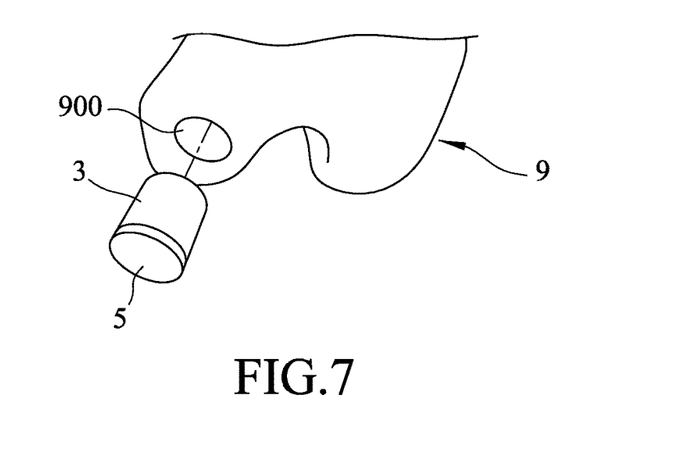
FIG. 7 is an exploded view illustrating implantation of the first embodiment of the bone implant into a hole of the bone structure.
Figure 8:
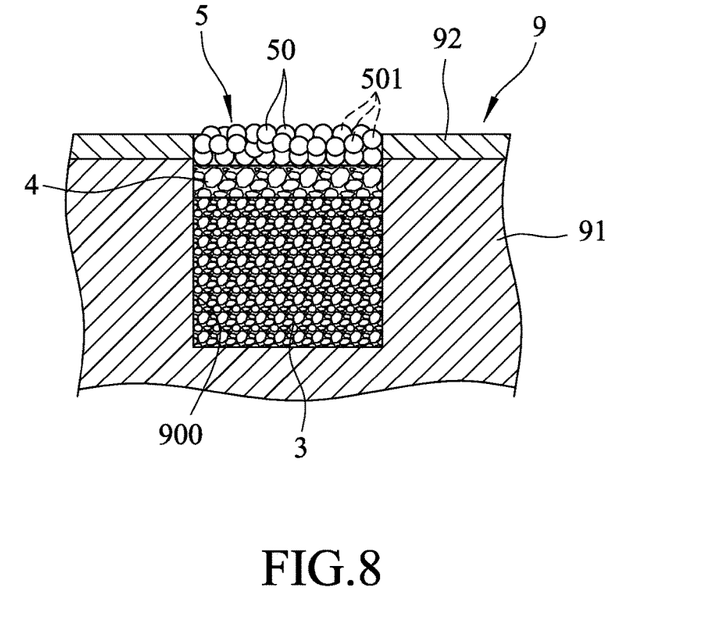
FIG. 8 is a fragmentary cross-sectional view illustrating the first embodiment of the bone implant implanted in a hole of the bone structure.

Referring to FIGS. 7 and 8, when the first embodiment of the bone implant is implanted in the hole 900 of the bone structure 9, the osteoblasts of the bone tissue 91 of the bone structure 9 will grow to fill pores of the scaffold 3, such that the scaffold 3 is securely fixed to the bone tissue 91 that is positioned in the hole 900. Moreover, chondroblasts and chondrocytes of the cartilage tissue 92 will also grow to fill the inner chambers 501 of the hollow microspheres 50 of the surface porous layer 5 so as to repair the cartilage tissue 92 of the bone structure 9. When the tissue-connecting portion 52 is made from collagen (as shown in FIG. 4), growth conditions for the chondrocytes will be improved and intercellular communication among the chondrocytes will be enhanced to ensure the chondrocytes' activity. Therefore, fibrosis of the grown cartilage tissue 92 will be decreased, so that the repair of the cartilage tissue 92 is enhanced.

In another configuration of first embodiment of the bone implant, the porous surface layer 5 may be composed of a plurality of stacked solid microspheres 50 and formed with a plurality of pores distributed among the stacked solid microspheres 50. When the bone implant is implanted in the hole 900 of the bone structure 9, the chondroblasts and the chondrocytes of the cartilage tissue 92 will grow to fill the pores of the porous surface layer 5 so as to achieve the repair of the cartilage tissue 92.

Figure 9:
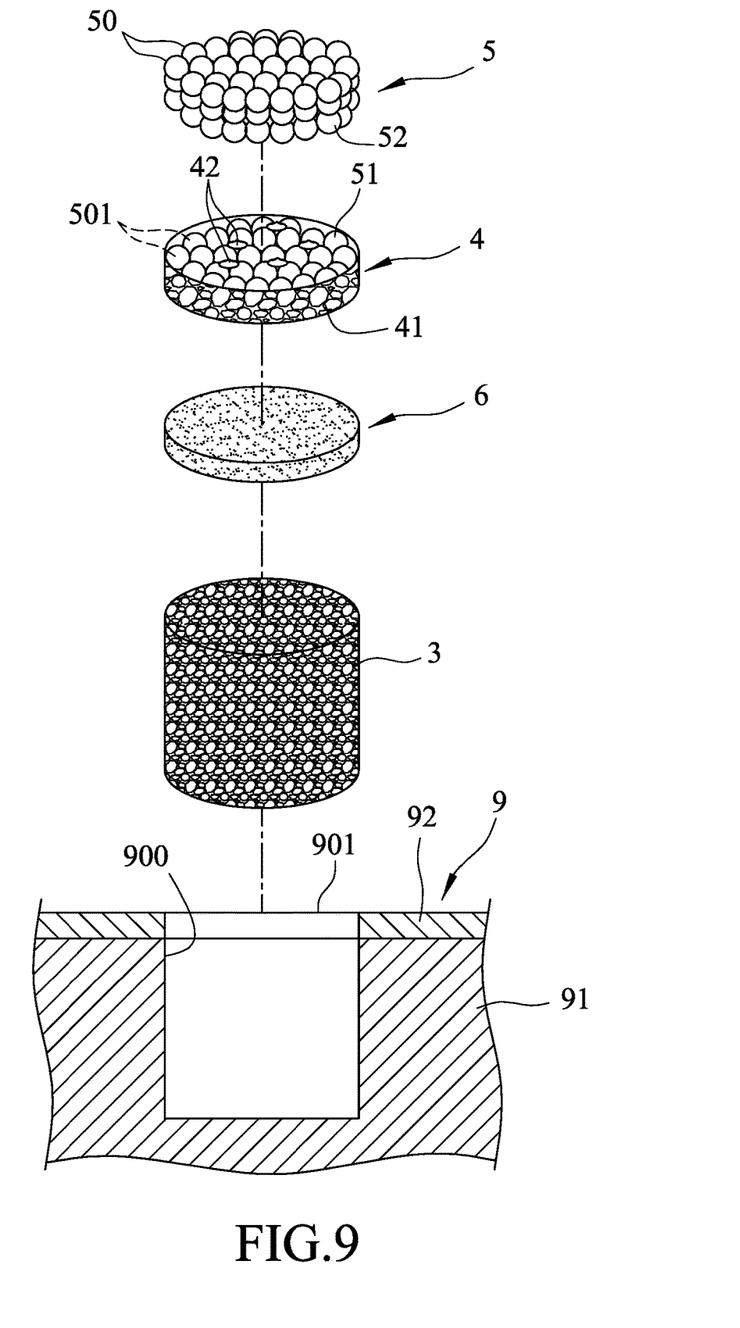
FIG. 9 is an exploded schematic view illustrating a second embodiment of a bone implant according to the disclosure.

Referring to FIG. 9, a second embodiment of the bone implant according to the disclosure is illustrated. In this embodiment, the bone implant further includes an isolating layer 6 disposed between the scaffold 3 and the connecting layer 4 so as to isolate the porous surface layer 5 from being in fluidic communication with the scaffold 3. The isolating layer 6 has a porosity smaller than those of the scaffold 3 and the connecting layer 4. In one form, the porosity of the isolating layer 6 ranges from 5% to 15%. More specifically, the porosity of the isolating layer 6 is 10%.

To be specific, by way of the design of the isolating layer 6 that has a relatively small porosity, tissue fluid generated from the degradation of the scaffold 3 is isolated and thus prevented from permeating into the porous surface layer 5. Consequently, the function of the porous surface layer 5 in facilitating the growth of the chondrocytes can be ensured.

To sum up, by virtue of the design of the scaffold 3 and the structure of the microspheres 50 of the porous surface layer 5 of the bone implant of this disclosure, the connection between the bone implant and the bone structure 9 is strengthened and the growth conditions of the cartilage tissue 92 are enhanced, thereby improving the efficiency of repairing the cartilage tissue 92.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A bone implant adapted to be implanted in a bone structure, the bone structure including a bone tissue and a cartilage tissue connected to the bone tissue, and being formed with a hole, the hole extending through the cartilage tissue and into the bone tissue and having an opening at the cartilage tissue, said bone implant comprising:
   a scaffold configured to be disposed in the hole of the bone structure for connecting with the bone tissue;
   a connecting layer disposed on said scaffold and proximal to the opening of the hole, said connecting layer including a bottom portion that is connected to said scaffold, and an extension portion that extends from said bottom portion in a direction away from said scaffold and that is formed with a plurality of receiving chambers; and
   a porous surface layer connected to said extension portion of said connecting layer, said porous surface layer including a plurality of filler portions that respectively fill said receiving chambers, and a tissue-connecting portion that is connected to the filler portions and configured for connecting with the cartilage tissue,
   wherein said porous surface layer is composed of a plurality of stacked hollow microspheres, each of said hollow microspheres having an inner chamber, the inner chambers of any two adjacent ones of said hollow microspheres being in spatial communication with each other.

2. The bone implant of claim 1, further comprising an isolating layer disposed between said scaffold and said connecting layer so as to isolate said porous surface layer from being in fluidic communication with said scaffold through said connecting layer.

3. The bone implant of claim 2, wherein said isolating layer has a porosity smaller than that of said scaffold and said connecting layer.

4. The bone implant of claim 3, wherein the porosity of said isolating layer ranges from 5% to 15%, the porosity of said scaffold ranging from 40% to 70%, the porosity of said connecting layer ranging from 60% to 70%.

5. The bone implant of claim 2, wherein said isolating layer is made from one of a porous biomedical material and a porous biological material, the porous biomedical material and the porous biological material being biodegradable and biocompatible.

6. The bone implant of claim 1, wherein said scaffold and said connecting layer are independently made from one of a porous biomedical material and a porous biological material, the porous biomedical material and the porous biological material being biodegradable and biocompatible.

7. The bone implant of claim 1, wherein said extension portion of said connecting layer includes a plurality of spaced-apart rod sections that respectively cooperate with said bottom portion to define said receiving chambers, and a plurality of retaining sections, each of said retaining sections being connected to an end of a respective one of said rod sections distal to said bottom portion.

8. The bone implant of claim 7, wherein each of said retaining sections is barb-shaped.

9. The bone implant of claim 1, wherein said porous surface layer is made from a biomedical material selected from the group consisting of a polymeric material, gelatine, collagen, and combinations thereof.

10. A bone implant adapted to be implanted in a bone structure, the bone structure including a bone tissue and a cartilage tissue connected to the bone tissue, and being formed with a hole, the hole extending through the cartilage tissue and into the bone tissue and having an opening at the cartilage tissue, said bone implant comprising:
    a scaffold configured to be disposed in the hole of the bone structure for connecting with the bone tissue;
    a connecting layer disposed on said scaffold and proximal to the opening of the hole, said connecting layer including a bottom portion that is connected to said scaffold, and an extension portion that extends from said bottom portion in a direction away from said scaffold and that is formed with a plurality of receiving chambers; and
    a porous surface layer connected to said extension portion of said connecting layer, said porous surface layer including a plurality of filler portions that respectively fill said receiving chambers, and a tissue-connecting portion that is connected to the filler portions and configured for connecting with the cartilage tissue,
    wherein said porous surface layer is composed of a plurality of stacked solid microspheres and formed with a plurality of pores distributed among said stacked solid microspheres.

11. The bone implant as claimed in claim 10, further comprising an isolating layer disposed between said scaffold and said connecting layer so as to isolate said porous surface layer from being in fluidic communication with said scaffold through said connecting layer.

12. The bone implant as claimed in claim 10, wherein said scaffold and said connecting layer are independently made from one of a porous biomedical material and a porous biological material, the porous biomedical material and the porous biological material being biodegradable and biocompatible.

13. The bone implant as claimed in claim 10, wherein said extension portion of said connecting layer includes a plurality of spaced-apart rod sections that respectively cooperate with said bottom portion to define said receiving chambers, and a plurality of retaining sections, each of said retaining sections being connected to an end of a respective one of said rod sections distal to said bottom portion.

14. The bone implant as claimed in claim 10, wherein said porous surface layer is made from a biomedical material selected from the group consisting of a polymeric material, gelatine, collagen, and combinations thereof.

15. A bone implant adapted to be implanted in a bone structure, the bone structure including a bone tissue and a cartilage tissue connected to the bone tissue, and being formed with a hole, the hole extending through the cartilage tissue and into the bone tissue and having an opening at the cartilage tissue, said bone implant comprising:
   a scaffold configured to be disposed in the hole of the bone structure for connecting with the bone tissue;
   a connecting layer disposed on said scaffold and proximal to the opening of the hole, said connecting layer including a bottom portion that is connected to said scaffold, and an extension portion that extends from said bottom portion in a direction away from said scaffold and that is formed with a plurality of receiving chambers;
   a porous surface layer connected to said extension portion of said connecting layer, said porous surface layer including a plurality of filler portions that respectively fill said receiving chambers, and a tissue-connecting portion that is connected to the filler portions and configured for connecting with the cartilage tissue, and
   an isolating layer disposed between said scaffold and said connecting layer so as to isolate said porous surface layer from being in fluidic communication with said scaffold through said connecting layer.

16. The bone implant as claimed in claim 15, wherein said porous surface layer is composed of a plurality of stacked hollow microspheres, each of said hollow microspheres having an inner chamber, said inner chambers of any two adjacent ones of said hollow microspheres being in spatial communication with each other.

17. The bone implant as claimed in claim 15, wherein said porous surface layer is composed of a plurality of stacked solid microspheres and formed with a plurality of pores distributed among said stacked solid microspheres.

18. The bone implant as claimed in claim 15, wherein said scaffold and said connecting layer are independently made from one of a porous biomedical material and a porous biological material, the porous biomedical material and the porous biological material being biodegradable and biocompatible.

19. The bone implant as claimed in claim 15, wherein said extension portion of said connecting layer includes a plurality of spaced-apart rod sections that respectively cooperate with said bottom portion to define said receiving chambers, and a plurality of retaining sections, each of said retaining sections being connected to an end of a respective one of said rod sections distal to said bottom portion.

20. The bone implant as claimed in claim 15, wherein said porous surface layer is made from a biomedical material selected from the group consisting of a polymeric material, gelatine, collagen, and combinations thereof.

\* \* \* \* \*